US012165760B2

(12) United States Patent
Fotouhi et al.

(10) Patent No.: US 12,165,760 B2
(45) Date of Patent: Dec. 10, 2024

(54) INTERACTIVE FLYING FRUSTUMS VISUALIZATION IN AUGMENTED REALITY

(71) Applicant: The Johns Hopkins University, Baltimore, MD (US)

(72) Inventors: Javad Fotouhi, Baltimore, MD (US); Mathias Unberath, Baltimore, MD (US); Nassir Navab, Fairfax, VA (US)

(73) Assignee: The Johns Hopkins University, Baltimore, MD (US)

( * ) Notice: Subject to any disclaimer, the term of this patent is extended or adjusted under 35 U.S.C. 154(b) by 635 days.

(21) Appl. No.: 17/310,746

(22) PCT Filed: Feb. 24, 2020

(86) PCT No.: PCT/US2020/019468
§ 371 (c)(1),
(2) Date: Aug. 20, 2021

(87) PCT Pub. No.: WO2020/176401
PCT Pub. Date: Sep. 3, 2020

(65) Prior Publication Data
US 2022/0139532 A1    May 5, 2022

Related U.S. Application Data

(60) Provisional application No. 62/810,132, filed on Feb. 25, 2019.

(51) Int. Cl.
*G01V 15/00* (2006.01)
*G06T 19/00* (2011.01)
(Continued)

(52) U.S. Cl.
CPC ........... *G16H 30/40* (2018.01); *G06T 19/006* (2013.01); *G06V 40/28* (2022.01); *G16H 10/60* (2018.01)

(58) Field of Classification Search
USPC ...... 128/915–925; 382/100–302; 704/1–275; 706/1, 62, 900–903
See application file for complete search history.

(56) References Cited

U.S. PATENT DOCUMENTS 10,929,670 B1 * 2/2021 Troy .................... G06V 20/653
2003/0029464 A1    2/2003 Chen et al.
(Continued)

FOREIGN PATENT DOCUMENTS

WO    2018/206086 A1    11/2018

OTHER PUBLICATIONS

Park an Jin; Device and Method for Medical Image Segmentation; 2017 (Year: 2017).*
(Continued)

*Primary Examiner* — Marcellus J Augustin
(74) *Attorney, Agent, or Firm* — Harrity & Harrity, LLP

(57) ABSTRACT

A device may receive, from an imaging device, a two-dimensional image of a patient being operated on by a user, where the two-dimensional image captures a portion of the patient, and where the portion of the patient is provided between a focal point of an imaging source of the imaging device and a detector plane of the imaging device. The device may translate the two-dimensional image along a frustum of the imaging source, and may generate one or more images in a three-dimensional space based on translating the two-dimensional image along the frustum of the imaging source. The device may provide the one or more images in the three-dimensional space to an augmented reality device associated with the user.

20 Claims, 15 Drawing Sheets

(51) Int. Cl.
*G06V 40/20* (2022.01)
*G16H 10/60* (2018.01)
*G16H 30/40* (2018.01)

(56) References Cited

U.S. PATENT DOCUMENTS

| | | | |
|---|---|---|---|
| 2003/0130576 A1* | 7/2003 | Seeley | A61B 90/36 |
| | | | 600/426 |
| 2015/0287236 A1 | 10/2015 | Winne et al. | |
| 2016/0225192 A1* | 8/2016 | Jones | G06T 19/20 |
| 2021/0153669 A1* | 5/2021 | Cato | E06B 9/24 |
| 2021/0169587 A1* | 6/2021 | Martin, III | A61B 34/20 |

OTHER PUBLICATIONS

Sebastian Andress; On-the-fly augmented reality for orthopedic surgery using a multimodal fiducial; 2018 (Year: 2018).*
Device and Method for Medical Image Segmentation; 2017 (Year: 2017).*
Sebastian Andress et al., "On-the-fly augmented reality for orthopedic surgery using a multimodal fiducial, " Conference Paper: Medical Imaging 2018, vol. 5(2), 13 Pages.
International Search Report and Written Opinion—PCT/US2020/019468—ISA/RU—May 25, 2020.

* cited by examiner

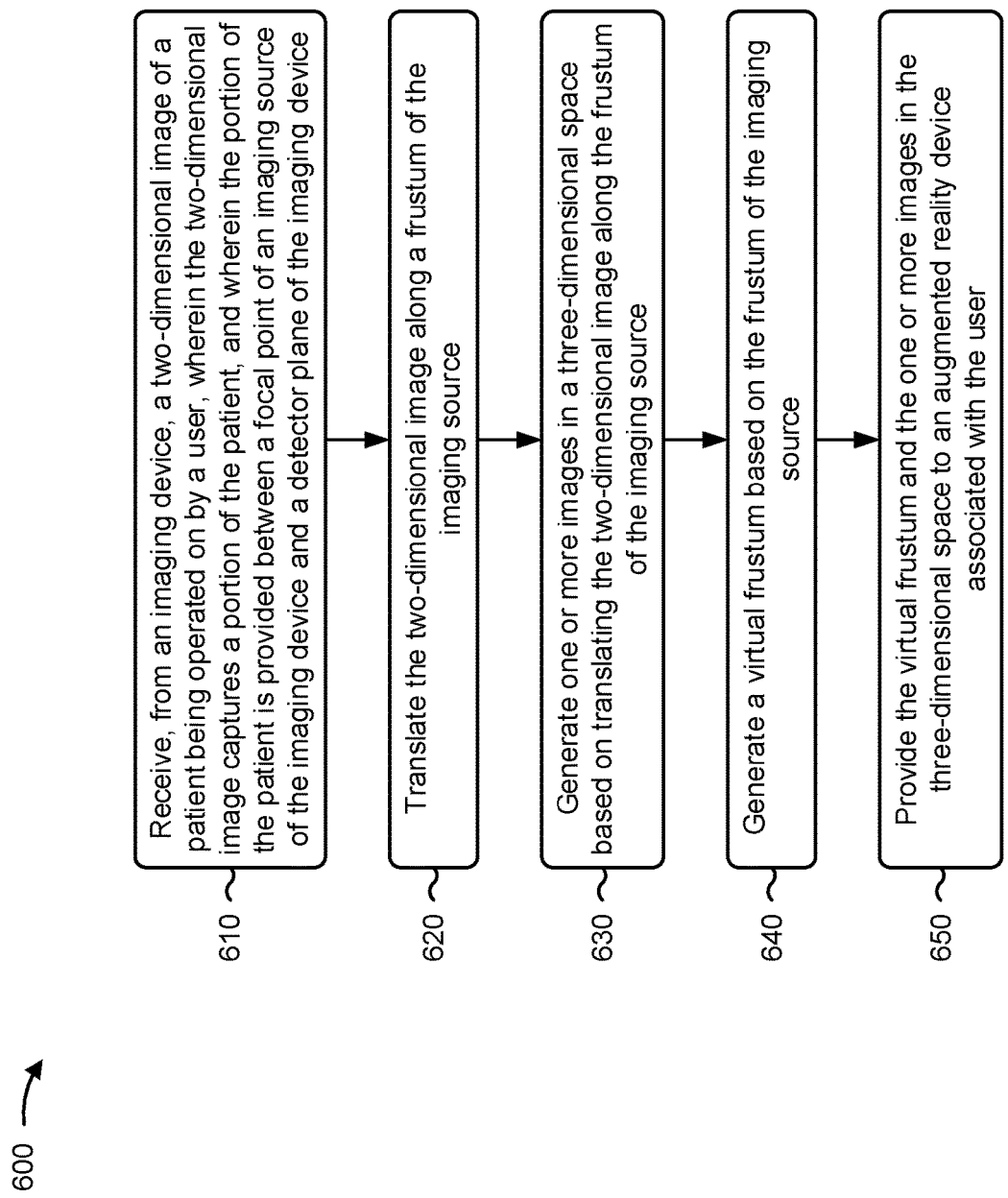

INTERACTIVE FLYING FRUSTUMS VISUALIZATION IN AUGMENTED REALITY

RELATED APPLICATIONS

This application is a 371 national stage of PCT Application PCT/US2020/019468 filed on Feb. 24, 2020, entitled "INTERACTIVE FLYING FRUSTUMS VISUALIZATION IN AUGMENTED REALITY," which claims priority to U.S. Provisional Patent Application No. 62/810,132, filed on Feb. 25, 2019, entitled "UTILIZING INTERACTIVE FLYING FRUSTUMS TO PROVIDE SPATIALLY-AWARE VISUALIZATION OF SURGICAL DATA IN AUGMENTED REALITY," both of which are hereby expressly incorporated by reference herein.

BACKGROUND

As the trend towards minimally invasive and percutaneous interventions continues for surgical procedures, the need for appropriate surgical data visualization becomes more and more evident. Ineffective interventional data display techniques yield poor ergonomics that hinder hand-eye coordination of a surgeon and promote frustration which can compromise a surgery and result in an adverse outcome. An example of ineffective visualization includes monitors attached to a base of mobile C-arm X-ray systems that are routinely used in orthopedic surgery (e.g., for C-arm fluoroscopy).

SUMMARY

According to some implementations, a method may include receiving, from an imaging device, a two-dimensional image of a patient being operated on by a user, wherein the two-dimensional image captures a portion of the patient, and wherein the portion of the patient is provided between a focal point of an imaging source of the imaging device and a detector plane of the imaging device. The method may include translating the two-dimensional image along a frustum of the imaging source, and generating one or more images in a three-dimensional space based on translating the two-dimensional image along the frustum of the imaging source. The method may include providing the one or more images in the three-dimensional space to an augmented reality device associated with the user.

According to some implementations, a device may include one or more memories, and one or more processors to receive, from an imaging device, a two-dimensional image of a patient being operated on by a user, wherein the two-dimensional image captures a portion of the patient, and wherein the portion of the patient is provided between a focal point of an imaging source of the imaging device and a detector plane of the imaging device. The one or more processors may translate the two-dimensional image along a frustum of the imaging source, and may generate one or more images in a three-dimensional space based on translating the two-dimensional image along the frustum of the imaging source. The one or more processors may provide the one or more images in the three-dimensional space to an augmented reality device associated with the user, and may receive, from the augmented reality device, a command associated with the one or more images in the three-dimensional space. The one or more processors may modify the one or more images in the three-dimensional space based on the command and to generate one or more modified images in the three-dimensional space, and may provide the one or more modified images in the three-dimensional space to the augmented reality device.

According to some implementations, a non-transitory computer-readable medium may store one or more instructions that, when executed by one or more processors of a device, may cause the one or more processors to receive, from an imaging device, a two-dimensional image of a patient being operated on by a user, wherein the two-dimensional image captures a portion of the patient, and wherein the portion of the patient is provided between a focal point of an imaging source of the imaging device and a detector plane of the imaging device. The one or more instructions may cause the one or more processors to translate the two-dimensional image along a frustum of the imaging source, and generate one or more images in a three-dimensional space based on translating the two-dimensional image along the frustum of the imaging source. The one or more instructions may cause the one or more processors to generate a virtual frustum based on the frustum of the imaging source, and provide the virtual frustum and the one or more images in the three-dimensional space to an augmented reality device associated with the user.

BRIEF DESCRIPTION OF THE DRAWINGS

FIGS. 4-6 are flow charts of example processes for utilizing interactive flying frustums to provide spatially-aware visualization of surgical data in augmented reality.

DETAILED DESCRIPTION

Figure 1A:
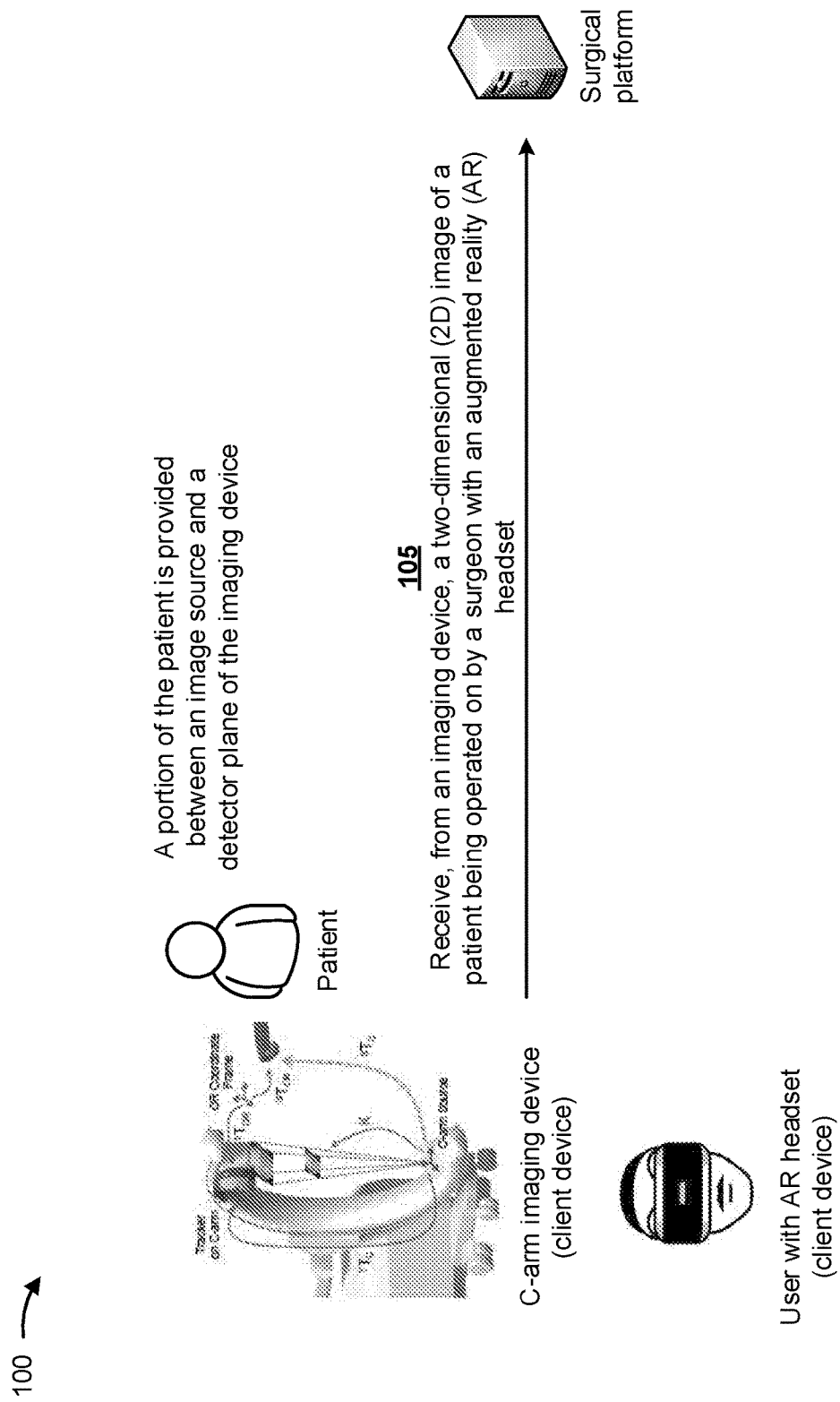
FIGS. 1A-1J are diagrams of one or more example implementations described herein.

The following detailed description of example implementations refers to the accompanying drawings. The same reference numbers in different drawings may identify the same or similar elements.

C-arm fluoroscopy is extensively used to guide minimally invasive surgery in a variety of clinical disciplines including neuro-radiology, orthopedics, trauma, and/or the like. Fluoroscopy provides real-time X-ray images that enable visualizing and monitoring the progress of a surgery on an anatomic level. In fracture care surgery, C-arm imaging is employed to guide the safe placement of implants, wires, screws, and/or the like. An example of fracture care surgery includes closed reduction and internal fixation of anterior pelvic fractures (e.g., fractures of superior pubic ramus). This procedure exhibits particularly small error margins due to close proximity of critical structures. To achieve required surgical accuracy and confidence, C-arm images are acquired from different views to verify acceptable tool trajectories. However, geometric interpretation of these interventional images is challenging and requires highly skilled and experienced surgeons that are trained to infer complex three-dimensional (3D) spatial relations from two-dimensional (2D) X-ray images. This requires "mental mapping" by the surgeon, which leads to acquisition of an excessive quantity of fluoroscopic images. The excessive quantity of fluoroscopic images may cause frustration for the surgeon, may compromise surgical efficiency, may result in procedural delays, may cause radiation hazards, and/or the like.

The complexity of interpreting 2D fluoroscopic images to establish spatial connections to the patient anatomy can, at least partly, be attributed to poor surgical ergonomics (e.g., due to inconvenient off-axis display of image data via external displays) and lack of geometric registration between image content and imaged anatomy. Thus, current C-arm fluoroscopy techniques waste computing resources (e.g., processing resources, memory resources, communication resources), networking resources, and/or the like associated with generating an excessive quantity of fluoroscopic images, reduced surgical efficiency, procedural delays, and/or the like.

Some implementations described herein may provide a surgical platform that utilizes interactive flying frustums (IFFs) to provide spatially-aware visualization of surgical data in augmented reality. For example, the surgical platform may receive, from an imaging device, a two-dimensional image of a patient being operated on by a user, where the two-dimensional image captures a portion of the patient, and where the portion of the patient is provided between a focal point of an imaging source of the imaging device and a detector plane of the imaging device. The surgical platform may translate the two-dimensional image along a frustum of the imaging source and may generate one or more images in a three-dimensional space based on translating the two-dimensional image along the frustum of the imaging source. The surgical platform may provide the one or more images in the three-dimensional space to an augmented reality device associated with the user.

In this way, the surgical platform may provide a spatially-aware approach to transmission image visualization that effectively unites patient anatomy with X-ray images by enabling spatial image manipulation that abides by image formation. The surgical platform may model a C-arm imaging geometry as a pinhole camera giving rise to a particular degree (e.g., an eleven degree) of freedom view frustum on which an X-ray image may be translated while remaining valid. Visualization of IFFs for the surgeon in an augmented reality environment may intuitively unite a virtual 2D X-ray image plane and a real 3D patient anatomy. To achieve this visualization, the surgical platform may track the surgeon (e.g., an AR headset of the surgeon) and the C-arm to the same coordinate frame using image-based localization and mapping. The surgical platform may be utilized for a variety of surgical tasks, such as surgical tasks that rely on orientational information (e.g., placing an acetabular component in total hip arthroplasty), and may pave the way for improving surgical performance and visuo-motor coordination in fluoroscopy-guided surgery. Thus, the surgical platform conserves computing resources (e.g., processing resources, memory resources, communication resources), networking resources, and/or the like that would otherwise be wasted in generating an excessive quantity of fluoroscopic images, reduced surgical efficiency, procedural delays, and/or the like.

FIGS. 1A-1J are diagrams of one or more example implementations 100 described herein. As shown in FIG. 1A, a C-arm imaging device (e.g., a client device shown in larger detail in FIG. 1E) and an augmented reality (AR) headset (e.g., a client device), worn by a user (e.g., a surgeon), may be associated with a surgical platform. The C-arm imaging device may capture X-ray images of a patient, may store the X-ray images of the patient, may provide the X-ray images to the surgical platform, and/or the like. In some implementations, another client device may be associated with the C-arm imaging device, may store the X-ray images of the patient, may provide the X-ray images to the surgical platform, and/or the like. In some implementations, a portion of the patient may be provided between an image source (e.g., an X-ray source) and a detector plane of the C-arm imaging device, as further shown in FIG. 1A. The surgical platform may include a platform that utilizes interactive flying frustums to provide spatially-aware visualization of surgical data in augmented reality, as described herein.

Although implementations are described herein as being performed by the surgical platform, implementations described herein may be performed by the C-arm imaging device, a client device associated with the C-arm imaging device, the AR headset, the surgical platform, and/or a combination of the aforementioned.

As further shown in FIG. 1A, and by reference number 105, the surgical platform may receive, from the C-arm imaging device (e.g., or the other client device), a two-dimensional (2D) image of the patient being operated on by the surgeon with the AR headset. In some implementations, the 2D image may include real-time X-ray images of the patient that enable visualizing and monitoring progress of the surgery on an anatomic level. In some implementations, the surgical platform may receive and store the X-ray images of the patient in a data structure (e.g., a database, a table, a list, and/or the like) associated with the surgical platform.

Figure 1B:
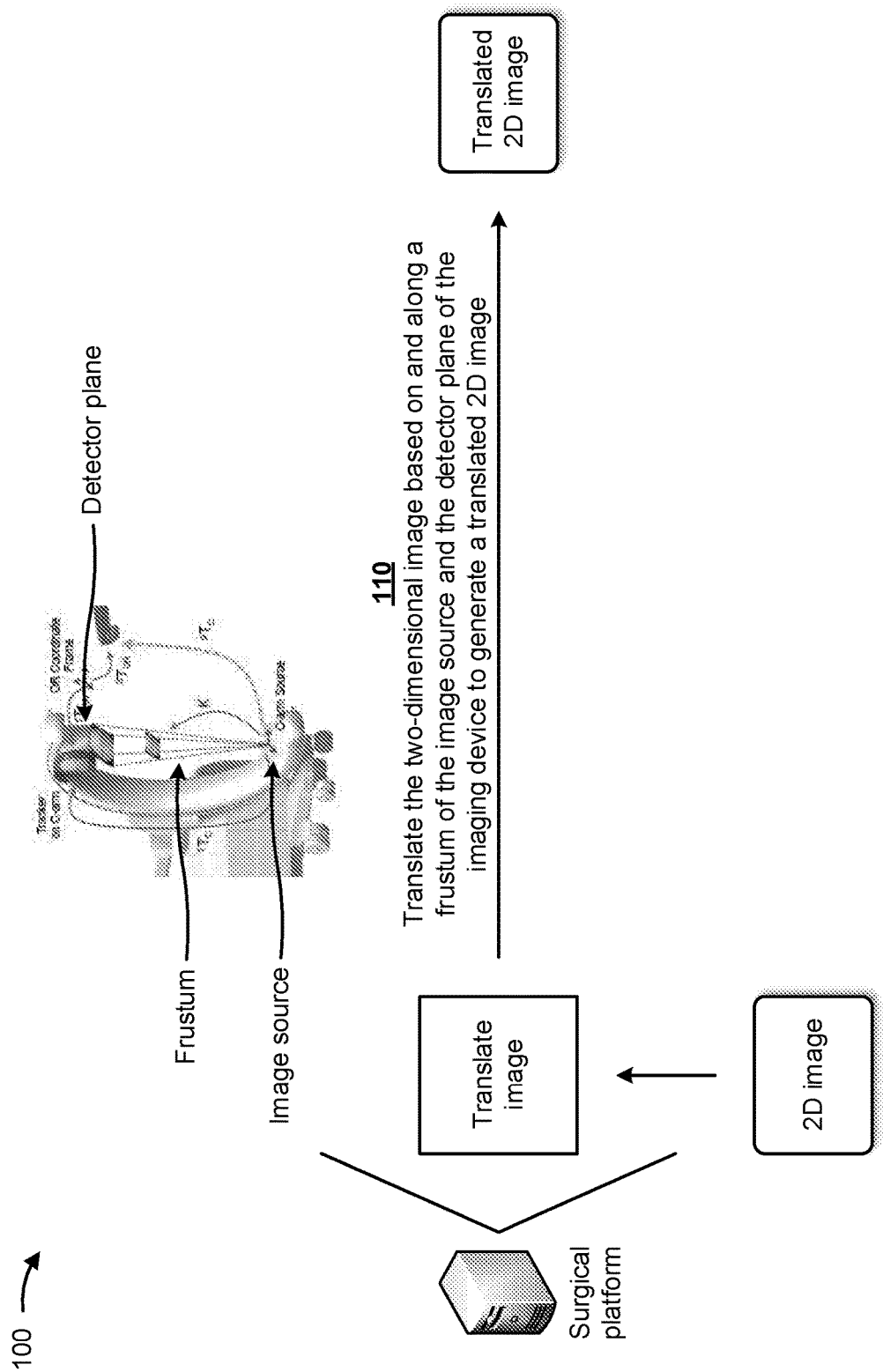

As shown in FIG. 1B, and by reference number 110, the surgical platform may translate the two-dimensional image based on and along a frustum of the image source and the detector plane of the C-arm imaging device to generate a translated two-dimensional image. In some implementations, the image source of the C-arm imaging device may generate X-rays that are received by the detector plane of the C-arm imaging device and generates the frustum (e.g., of the X-rays).

In some implementations, X-ray image formation by the C-arm imaging device may be geometrically described by a pinhole camera model with the X-ray source constituting a focal point. In contrast to optical imaging, which relates to reflected light quanta, X-ray imaging measures transmitted intensity. As a consequence, an object may be placed between a focal spot (e.g., the X-ray source) and the detector plane of the C-arm imaging device. Given particular degree of freedom (e.g., eleven degrees) camera parameters, the frustum may describe a cone of vision (or a pyramid of vision) centered at the focal point, with an active area of the detector plane defining a base. When the detector plane is normal to a principal X-ray of the C-arm imaging device, any image acquired in this fixed C-arm pose may be translated along a z-axis of the C-arm imaging device (e.g., along the frustum), while remaining a valid image of the same 3D scene.

In transmission imaging, this property of the frustum may be beneficial because near and far planes of the frustum may be held constant at z=0 and z=DSD (e.g., where DSD is a source-to-detector distance). In other words, there is no need for adaptive frustum culling since every location on a trajectory of any frustum point may have contributed to an intensity of that point. Consequently, for every structure that is prominent in an X-ray image (e.g., a bone contour), there may be a well-defined position z on the frustum, where that image region coincides with the generating anatomical structure. The surgical platform may utilize this property to unite and augment the patient with 2D X-ray images acquired in arbitrary geometry. This augmented view onto anatomy may be realized using an AR environment that is delivered to the surgeon via the AR headset.

Figure 1C:
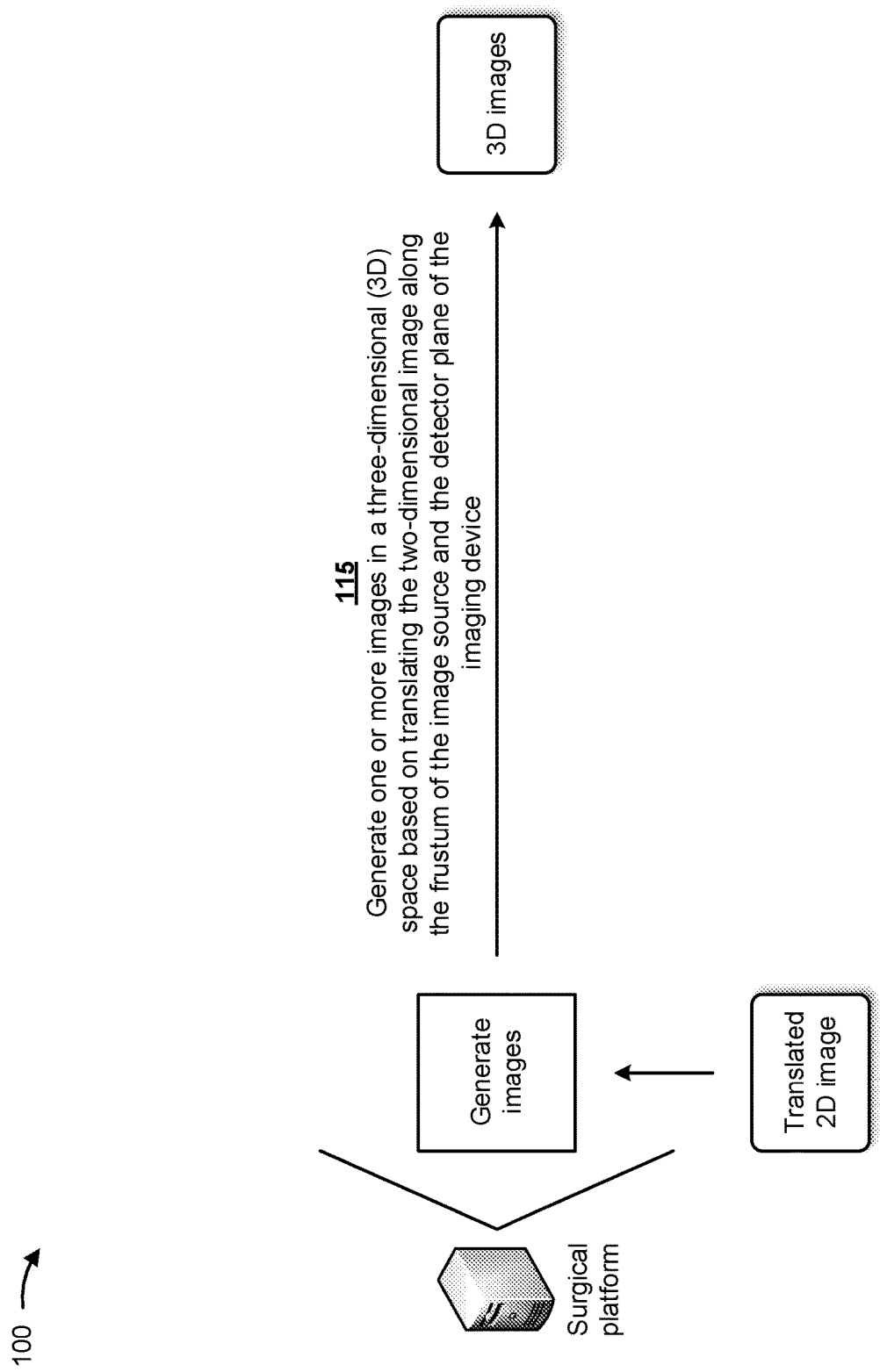

As shown in FIG. 1C, and by reference number 115, the surgical platform may generate one or more images in a three-dimensional (3D) space based on translating the two-dimensional image along the frustum of the image source and the detector plane of the imaging device. For example, as described above, since the detector plane of the C-arm imaging device is normal to the image source of the C-arm imaging device, any image acquired in this fixed C-arm pose may be translated along a z-axis of the C-arm imaging device (e.g., along the frustum), while remaining a valid image of the same 3D scene.

Figure 1D:
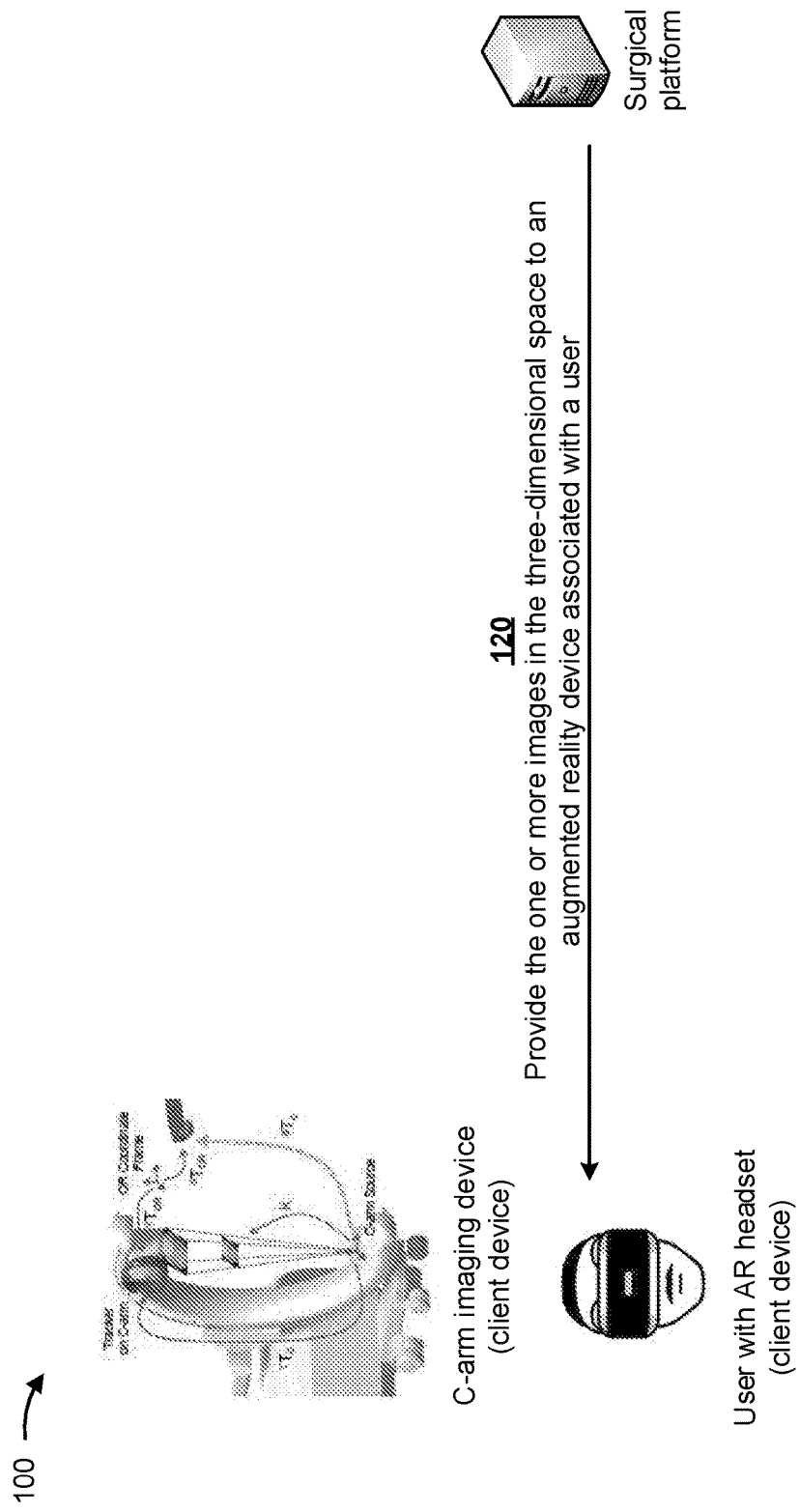

As shown in FIG. 1D, and by reference number 120, the surgical platform may provide the one or more images in the three-dimensional space to an augmented reality device (e.g., the AR headset) associated with a user (e.g., the surgeon). In some implementations, the one or more images in the three-dimensional space may include augmented reality information that is based on the interactive flying frustums. In some implementations, the surgical platform may provide the augmented reality information (e.g., the one or more images in the three-dimensional space), with the real-time X-ray images, to the AR headset of the surgeon.

In some implementations, the surgical platform may enable the surgeon to instantaneously observe all acquired X-ray images (e.g., by the C-arm imaging device) at a position of a detector at the moment the X-ray images are acquired. The surgical platform may enable the surgeon to interactively move an X-ray image within a geometrical frustum passing through an actual anatomy of the patient, and may enable the surgeon to point to a position of the X-ray image at a particular point during the surgery and ask associates to bring the C-arm imaging device to that position. The surgical platform may enable the associates of the surgeon to observe the same floating imagery data and the corresponding position of the C-arm imaging device.

In some implementations, the surgical platform may enable the surgeon to review all X-ray image acquisitions with corresponding spatial and temporal acquisition information. The surgical platform may provide a new AR methodology that leverages the concept of a view frustum combined with improved dynamic inside-out calibration of the C-arm imaging device for the AR environment and for spatially-aware visualization. The surgical platform may display medical images at a surgical site, which overcomes the challenges introduced by off-axis display, and may effectively and implicitly calibrate acquired fluoroscopic images of the patient by allowing the images to slide along the viewing frustum.

Figure 1E:
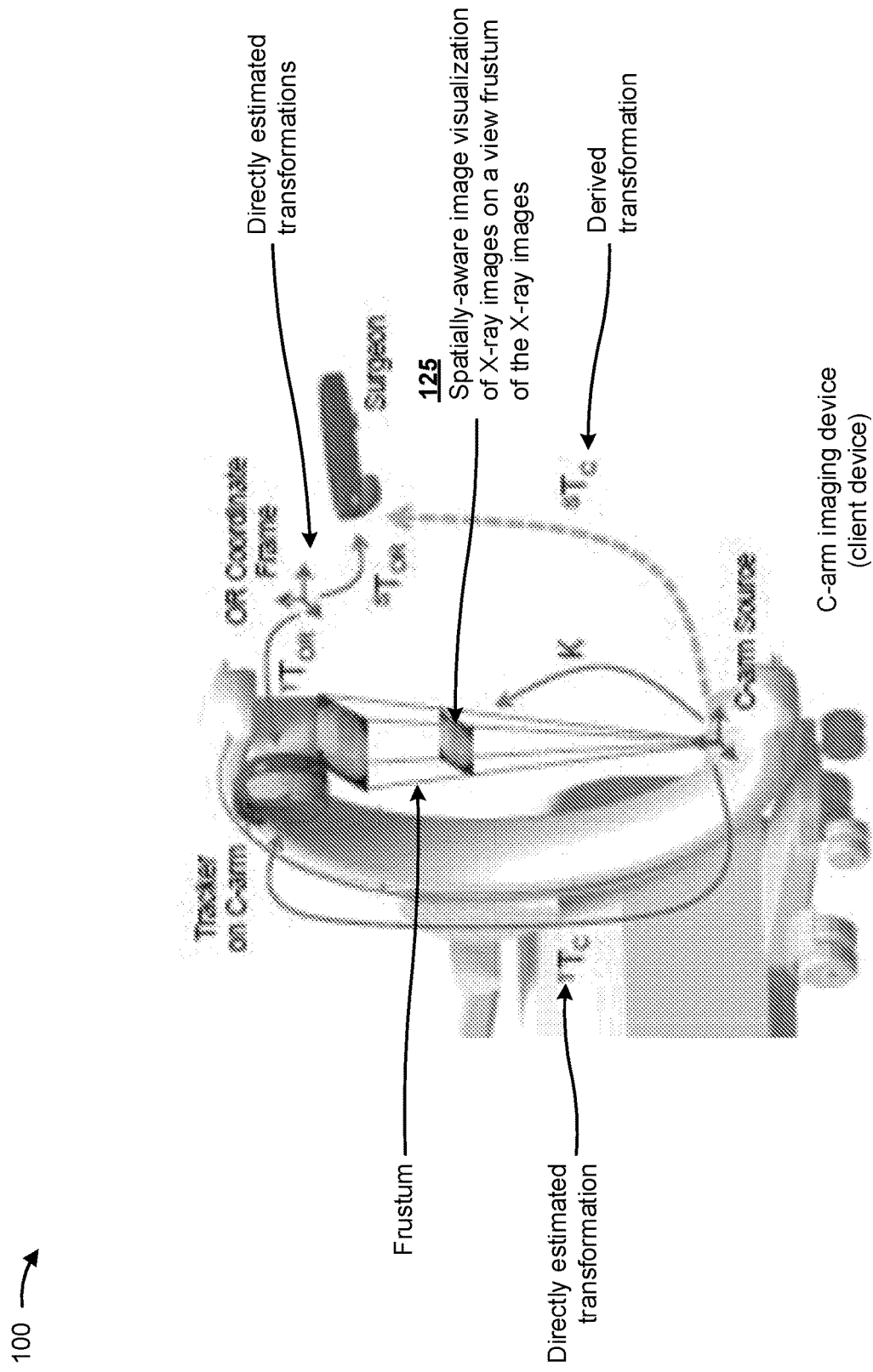

As shown in FIG. 1E, and by reference number 125, the surgical platform may provide (e.g., via the C-arm imaging device) a spatially-aware image visualization of X-ray images on a frustum of X-ray images. As further shown in FIG. 1E, the surgical platform may provide (e.g., via the C-arm imaging device) estimated transformations (e.g., estimated dynamically) that enable the AR environment for the AR headset. Transformations shown as solid arrows may be directly estimated transformations, while a transformation shown as a dashed arrow may be a derived transformation.

Figure 1F:
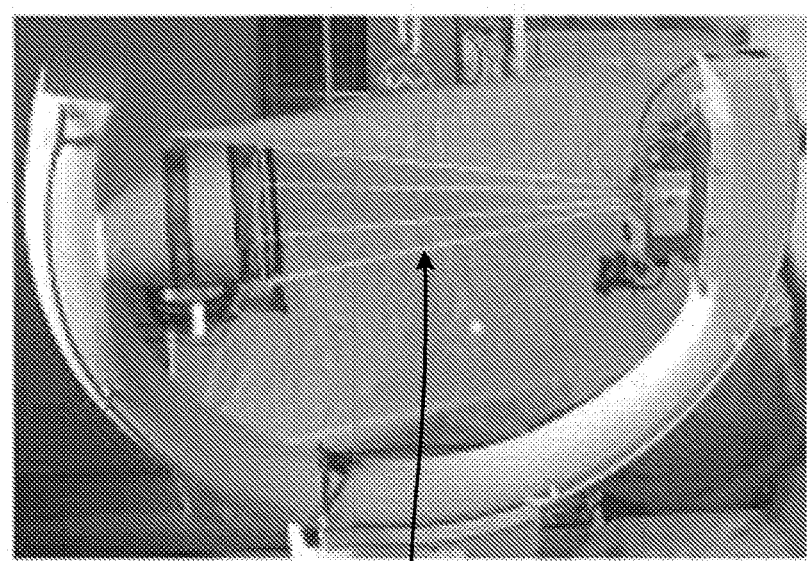
Figure 1G:
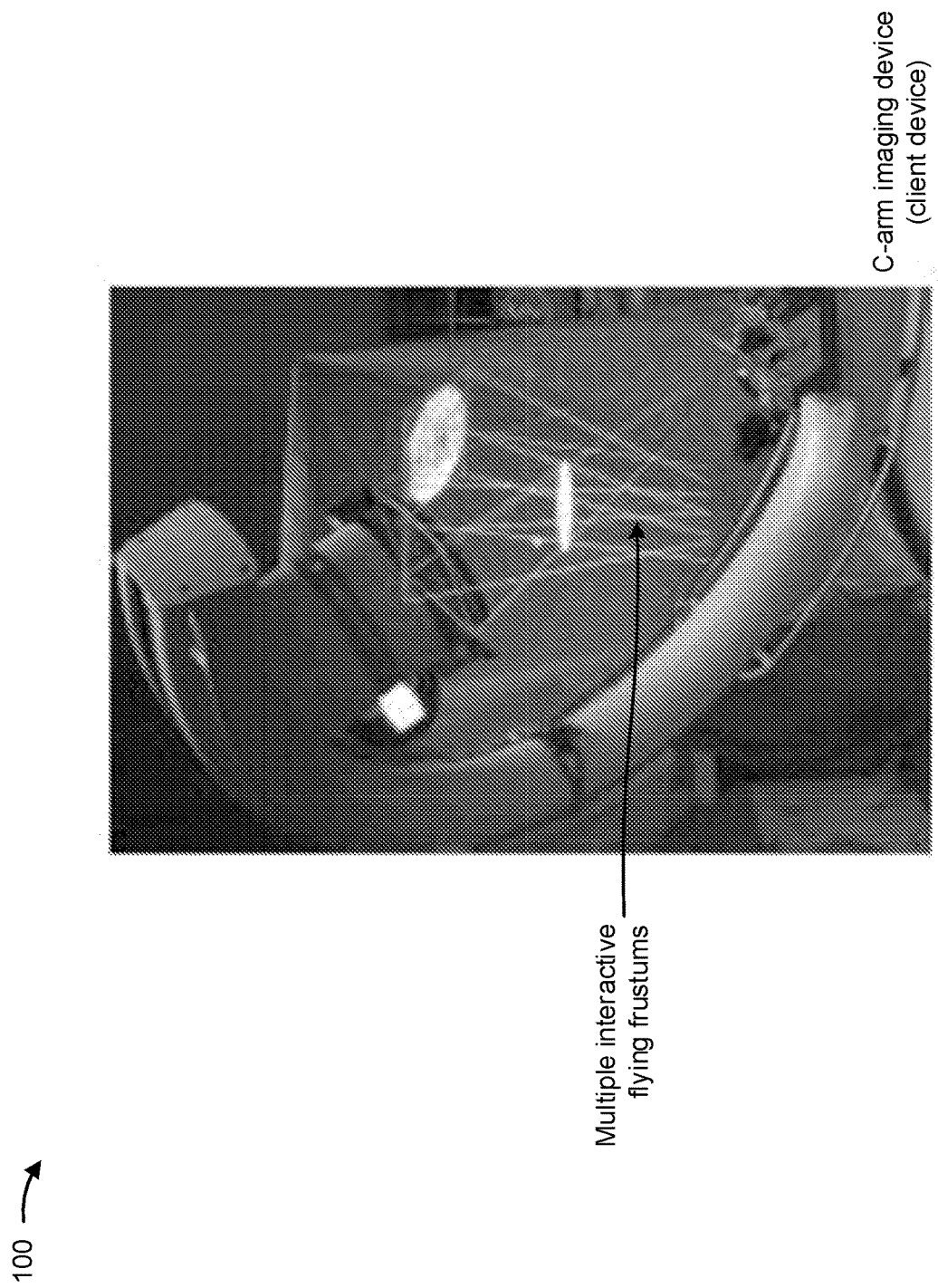

FIG. 1F demonstrates use of a single interactive flying frustum provide by the C-arm imaging device. FIG. 1G demonstrates a simultaneous visualization of multiple (e.g., three) interactive flying frustums by the C-arm imaging device. In some implementations, the C-arm imaging device may provide one or more interactive flying frustums.

Figure 1H:
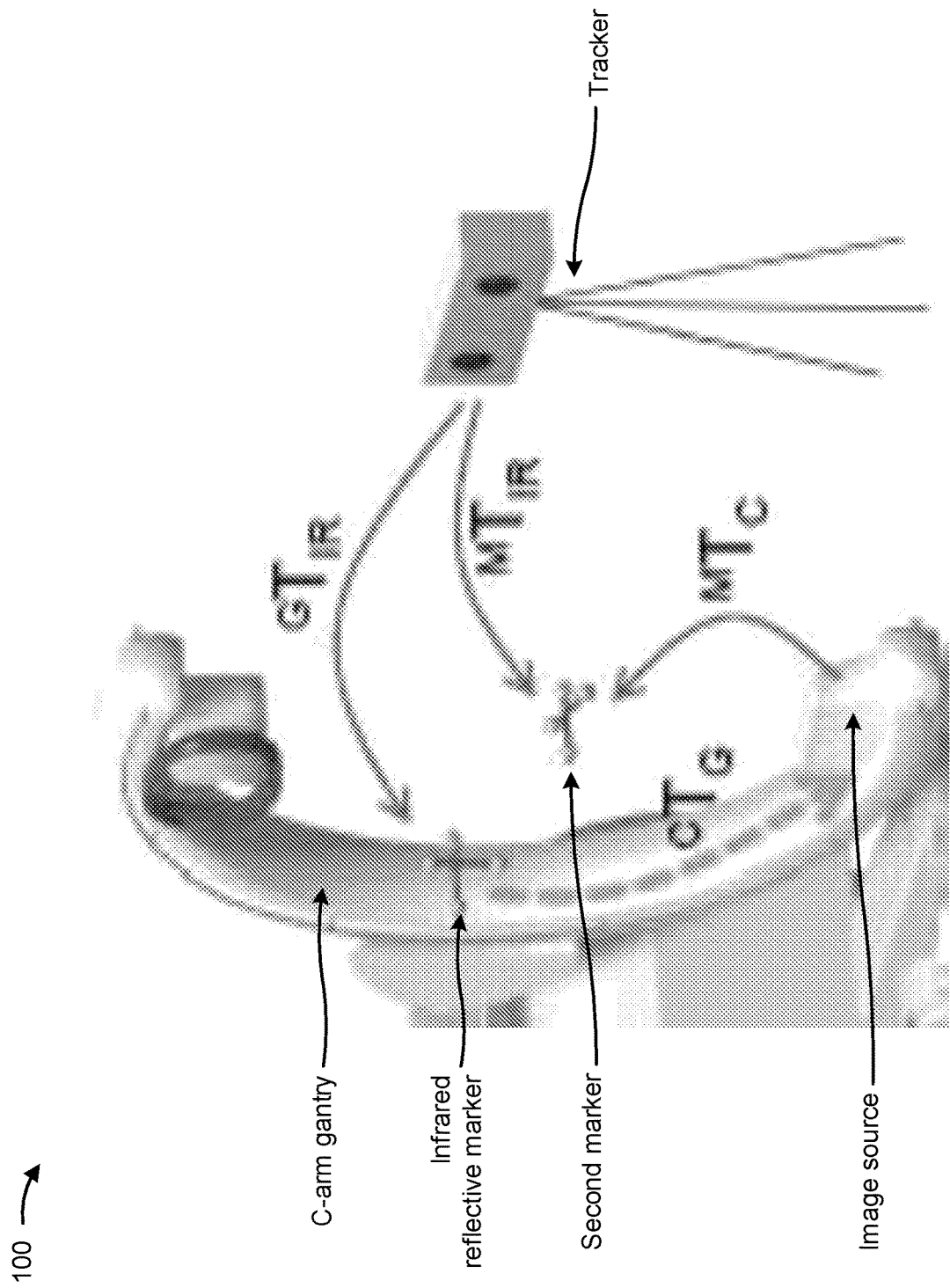
Figure 1I:
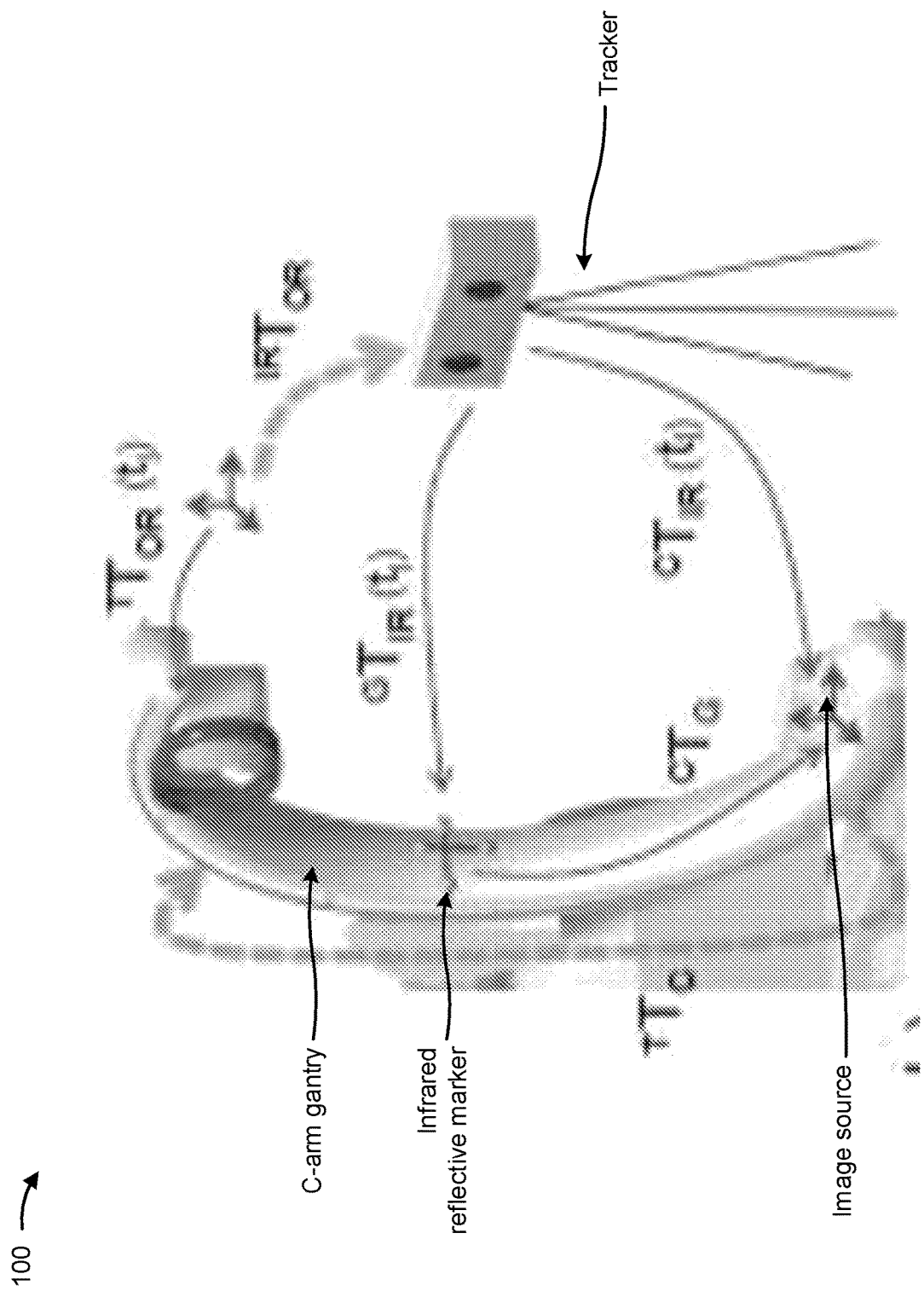
Figure 1J:
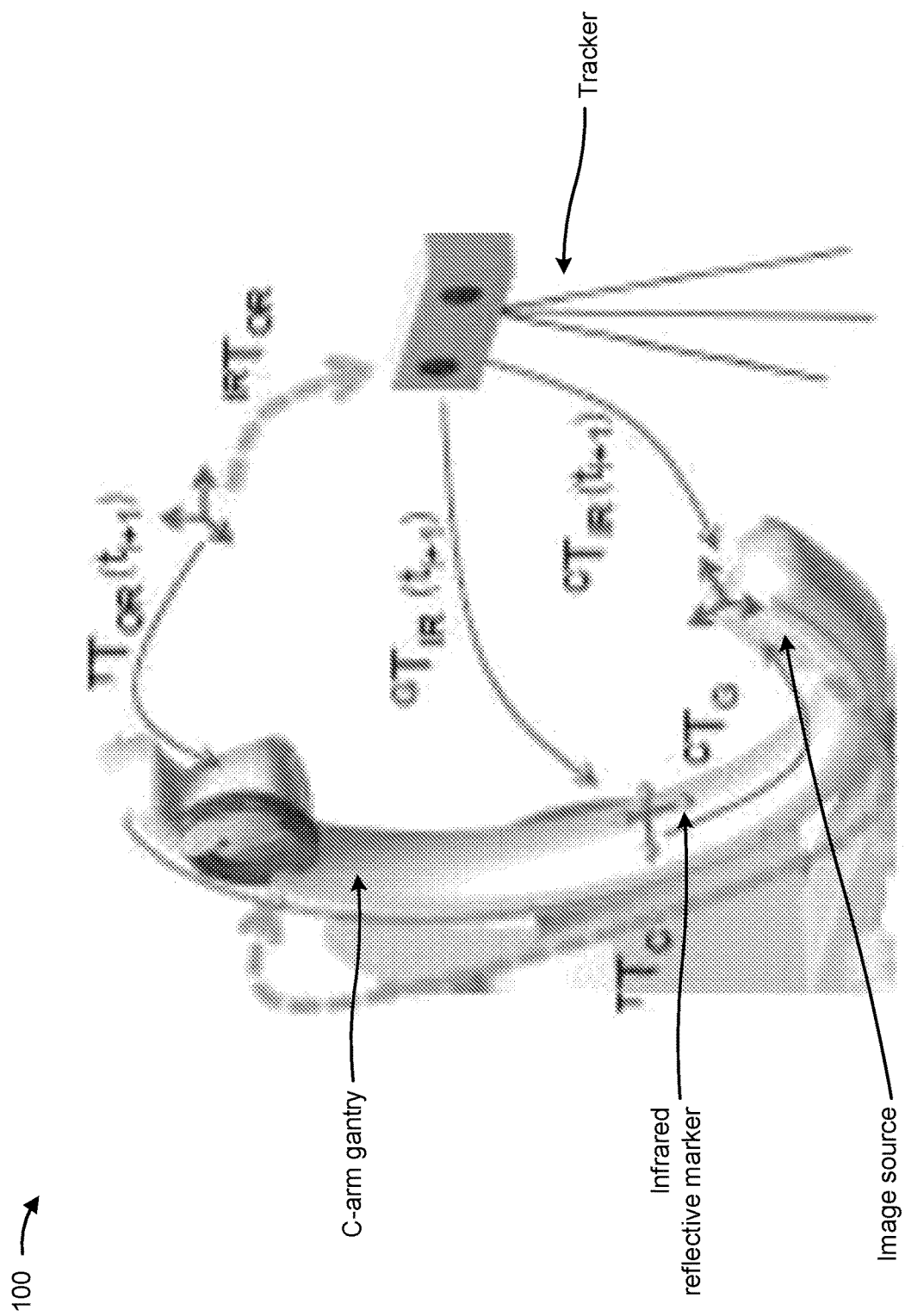

FIGS. 1H-1J illustrate a process of calibrating a tracker to the C-arm imaging device using hand-eye calibration and an external optical navigation system. In some implementations, the surgical platform may be utilized to calibrate the tracker to the C-arm imaging device. As shown in FIG. 1H, an infrared reflective marker may be attached to a C-arm gantry and may be calibrated to an image source (e.g., an X-ray source) of the C-arm imaging device using a second marker that is imaged by the optical navigation system and the C-arm imaging device simultaneously. As shown in FIGS. 1I and 1J, the C-arm gantry, the infrared reflective marker, and/or the tracker may be moved, and corresponding pose pairs in respective frames of a reference may be collected (e.g., by the surgical platform), which may be utilized for hand-eye calibration.

In order to realize the AR visualization of X-ray images in a spatially-aware manner, a pose of the C-arm imaging device defining the corresponding view frustum must be known in a coordinate system of the AR headset delivering the AR experience. To this end, the surgical platform may utilize an approach that is marker-less and radiation-free, and that utilizes vision-based inside-out tracking to dynamically close a calibration loop. Inside-out tracking may require both the surgeon and the C-arm imaging device to navigate a same environment (e.g., an operating room), which may be referred to as an "OR coordinate system." For interventional visualization of X-ray images using IFFs, the surgical platform may recover:

$$^{S}T_C(t) = {^{S}T_{OR}(t)}({^{T}T_{OR}^{-1}(t)}{^{T}T_C(t_0)}) \tag{1}$$

which is a transformation describing a mapping from a C-arm image source coordinate to the surgeon's eyes as both the C-arm image source and the surgeon move within the environment over time (t). In Equation 1, $t_0$ may describe a time of offline calibration. Upon acquisition of an X-ray image ($I_i$) at time $t_i$, $^{OR}T_C(t_i)$ may be held constant, since a viewpoint of the corresponding frustum may not be altered and only translation of the image along a respective z-axis is permitted. The spatial relations that are required to dynamically estimate $^{S}T_C(t)$ are further explained below.

For inside-out tracking of the surgeon and the tracker on the C-arm (e.g., $^{OR}T_{S/T}$), vision-based simultaneous localization and mapping (SLAM) may be used to incrementally build a map of the environment and estimate a camera's pose $^{OR}T_{S/T}$ therein. Using the surgeon as an example, SLAM may solve the following:

$$^{OR}T_S(t) = \underset{^{OR}T_S}{\operatorname{argmin}} \, d\big(f_{OR}\big(P^{OR}T_S(t)x_S(t)\big), f_S(t)\big) \tag{2}$$

where $f_S(t)$ may include features extracted from the image at time t, $x_S(t)$ may include the 3D locations of these feature obtained via a multi-view stereo, P may include a projection operator, and d may include a similarity to be optimized. The C-arm gantry may be tracked relative to the exact same map of the environment by rigidly attaching an additional tracker to the C-arm gantry. To this end, both trackers may be the same make and model, and may operate in a master-slave configuration. The environmental map provided by the master on start-up of the slave may exhibit partial overlap with the current field of view of the slave tracker (e.g., a feature rich and temporally stable area of the environment). As a consequence, cameras of the C-arm tracker may be oriented such that they face the operating room and not the surgical site.

For one-time offline calibration of tracker to C-arm source (e.g., $^{T}T_{C}(t_0)$), since the fields of view of the tracker and the X-ray source do not share overlap, it may not be feasible to co-register these sensors via a common calibration phantom. Alternatively, the surgical platform may estimate $^{T}T_{C}(t_0)$ via hand-eye calibration (e.g., where relative pose information from the rigidly connected tracker and the C-arm may be used for solving $X:=^{T}T_{C}(t_0)$ in $AX=XB$ fashion. To construct this over-determined system, the C-arm imaging device may undergo different motions along the degrees of freedom, and corresponding relative pose information of the tracker and the C-arm source may be stored in A and B matrices, respectively.

Since current C-arms do not exhibit encoded joints, the surgical platform may rely on optical infrared tracking to estimate the pose of the C-arm source. To this end, passive markers M may be introduced into the X-ray field of view, and another set of reflective markers G may be rigidly attached to the C-arm gantry. The spatial link between the C-arm gantry and the C-arm source may be estimated via the following equation:

$$^{C}T_{G} = {}^{M}T_{C}^{-1} \, {}^{M}T_{IR} \, {}^{G}T_{IR}^{-1} \tag{3}$$

where $^{M}T_{C}^{-1}$ may be rigid extrinsic parameters expressing the source to marker configuration. To estimate this transformation, spherical marker locations may be automatically identified in X-ray images via a circular Hough transform. Once $^{M}T_{C}^{-1}$ is estimated, marker M may be removed and the C-arm pose may be estimated in a frame of the external optical navigation system $^{C}T_{IR} = {}^{C}T_{G} \, {}^{G}T_{IR}$. To solve the calibration problem in a hand-eye configuration, the surgical platform may construct the following chain of transformations:

$$^{T}T_{OR}^{-1}(t_i) {}^{T}T_{C}(t_0) {}^{C}T_{IR}(t_i) = {}^{T}T_{OR}^{-1}(t_{i+1}) {}^{T}T_{C}(t_0) {}^{C}T_{IR}(t_{i+1})$$

$$^{T}T_{OR}(t_{i+1}) {}^{T}T_{OR}^{-1}(t_i) {}^{T}T_{C}(t_0) = {}^{T}T_{C}(t_0) {}^{C}T_{IR}(t_{i+1}) {}^{C}T_{IR}^{-1}(t_i) \tag{4}$$

Equation 4 expresses relations for poses acquired at times $t_i$ and $t_{i-1}$. The surgical platform may decouple rotation $R_x$ and translation $p_x$ parameters. The rotation parameters may be estimated using a unit quaternion representation $Q_x$ as follows:

$$Q_a Q_x = Q_x Q_b \tag{5}$$

By re-arranging Equation 5 in the form of $MQ_x=0$, the surgical platform may solve for rotation in the following constrained optimization:

$$\min \|MQ_x\|_2^2, \text{ such that } \|Q_x\|_2^2 = 1 \tag{6}$$

Finally, the translation component $p_x$ may be estimated in a least-squares fashion as expressed in Equation 7, where R may represent a rotation matrix:

$$R_a p_x + p_a \approx R_x p_b + p_x,$$

$$(R_a - 1) p_x \approx R_x p_b - p_a \tag{7}$$

The view frustum of the C-arm imaging device may be modeled via eleven degrees of freedom camera parameters. Details for computing six degrees of freedom extrinsic parameters $^{T}T_{C}(t)$ relative to the surgeon required for visualization are described above. The remaining five degrees of freedom intrinsic parameters (K) may be associated with focal length, pixel spacing, skew, and principle point that are available from internal calibration of the C-arm imaging device and may be provided by a manufacturer of the C-arm imaging device. Given these eleven parameters, interactive flying frustums (IFFs) may be rendered in the AR environment.

Interaction with the virtual frustum of the X-ray image in the AR surgery environment may be built upon a surgeon's gaze, hand gesture, voice commands, and/or the like. An intersection of a gaze ray and a virtual object may be used as a mechanism to select and highlight an X-ray image that, potentially, may be minimized to a point in a focal point location. The X-ray image may be manipulated with a single degree of freedom to slide along the z-axis through the frustum following the surgeon's hand gestures that are detected by gesture-sensing cameras on the AR headset. The virtual frustum may be rendered in a particular color (e.g., red) as the X-ray image reaches the image source, and in another particular color (e.g., green) as the image approaches the image detector. Finally, voice commands, such as "lock" and "unlock" may allow the surgeon to lock and unlock the pose of the virtual image, and the use of the voice command "next" may highlight a next acquired X-ray image within the corresponding frustum.

In this way, the surgical platform utilizes interactive flying frustums to provide spatially-aware visualization of surgical data in augmented reality, which conserves computing resources (e.g., processing resources, memory resources, communication resources, and/or the like), networking resources, hospital resources (e.g., a heart monitor, a breathing apparatus, and/or the like), and/or the like, that would otherwise be wasted in generating an excessive quantity of fluoroscopic images, reduced surgical efficiency, procedural delays, and/or the like.

As indicated above, FIGS. 1A-1J are provided merely as examples. Other examples may differ from what is described with regard to FIGS. 1A-1J. The number and arrangement of devices shown in FIGS. 1A-1J are provided as an example. In practice, there may be additional devices, fewer devices, different devices, or differently arranged devices than those shown in FIGS. 1A-1J. Furthermore, two or more devices shown in FIGS. 1A-1J may be implemented within a single device, or a single device shown in FIGS. 1A-1J may be implemented as multiple, distributed devices. Additionally, or alternatively, a set of devices (e.g., one or more devices) of FIGS. 1A-1J may perform one or more functions described as being performed by another set of devices of FIGS. 1A-1J.

Figure 2:
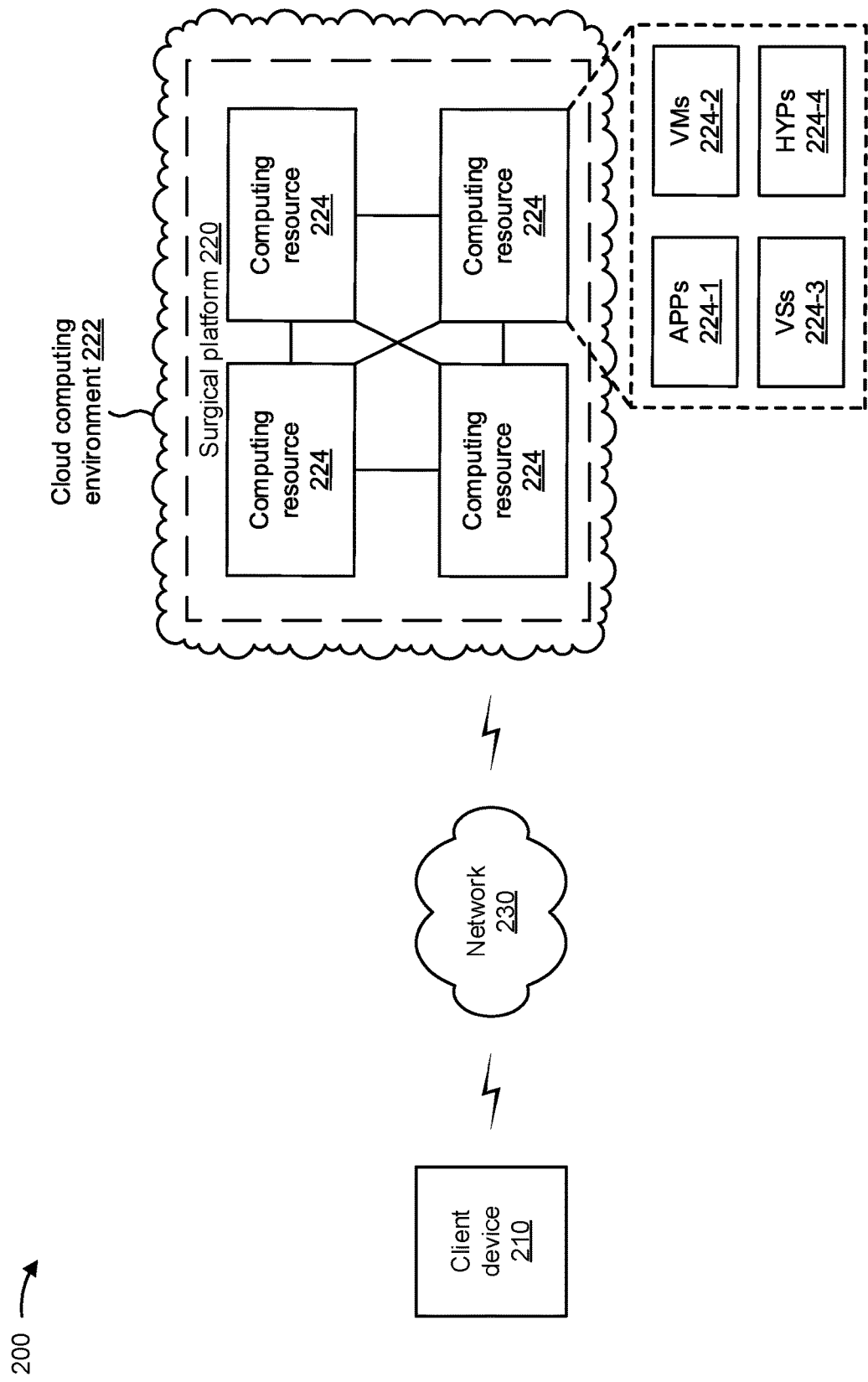
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a client device 210, a surgical platform 220, and a network 230. Devices of environment 200 may interconnect via wired connections, wireless connections, or a combination of wired and wireless connections.

Client device 210 includes one or more devices capable of receiving, generating, storing, processing, and/or providing information, such as information described herein. For example, client device 210 may include a mobile phone (e.g., a smart phone, a radiotelephone, and/or the like), a laptop computer, a tablet computer, a desktop computer, a handheld computer, a set-top box, a gaming device, a wearable communication device (e.g., a smart watch, a pair of smart glasses, a heart rate monitor, a fitness tracker, smart clothing, smart jewelry, a head mounted display, an AR headset, and/or the like), an imaging device (e.g., C-arm imaging device), or a similar type of device. In some implementations, client device 210 may receive information from and/or transmit information to surgical platform 220.

Surgical platform 220 includes one or more devices that utilize interactive flying frustums to provide spatially-aware visualization of surgical data in augmented reality. In some implementations, surgical platform 220 may be designed to be modular such that certain software components may be swapped in or out depending on a particular need. As such, surgical platform 220 may be easily and/or quickly reconfigured for different uses. In some implementations, surgical platform 220 may receive information from and/or transmit information to one or more client devices 210.

In some implementations, as shown, surgical platform 220 may be hosted in a cloud computing environment 222. Notably, while implementations described herein describe surgical platform 220 as being hosted in cloud computing environment 222 (e.g., a data center), in some implementations, surgical platform 220 may not be cloud-based (i.e., may be implemented outside of a cloud computing environment) or may be partially cloud-based.

Cloud computing environment 222 includes an environment that hosts surgical platform 220. Cloud computing environment 222 may provide computation, software, data access, storage, etc., services that do not require end-user knowledge of a physical location and configuration of system(s) and/or device(s) that host surgical platform. As shown, cloud computing environment 222 may include a group of computing resources 224 (referred to collectively as "computing resources 224" and individually as "computing resource 224").

Computing resource 224 includes one or more personal computers, workstation computers, mainframe devices, or other types of computation and/or communication devices. In some implementations, computing resource 224 may host surgical platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by client device 210. Application 224-1 may eliminate a need to install and execute the software applications on client device 210. For example, application 224-1 may include software associated with surgical platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system. A process virtual machine may execute a single program and may support a single process. In some implementations, virtual machine 224-2 may execute on behalf of a user (e.g., a user of client device 210 or an operator of surgical platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks. In some implementations, network 230 may receive information from and/or transmit information to client device 210 and/or surgical platform 220.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
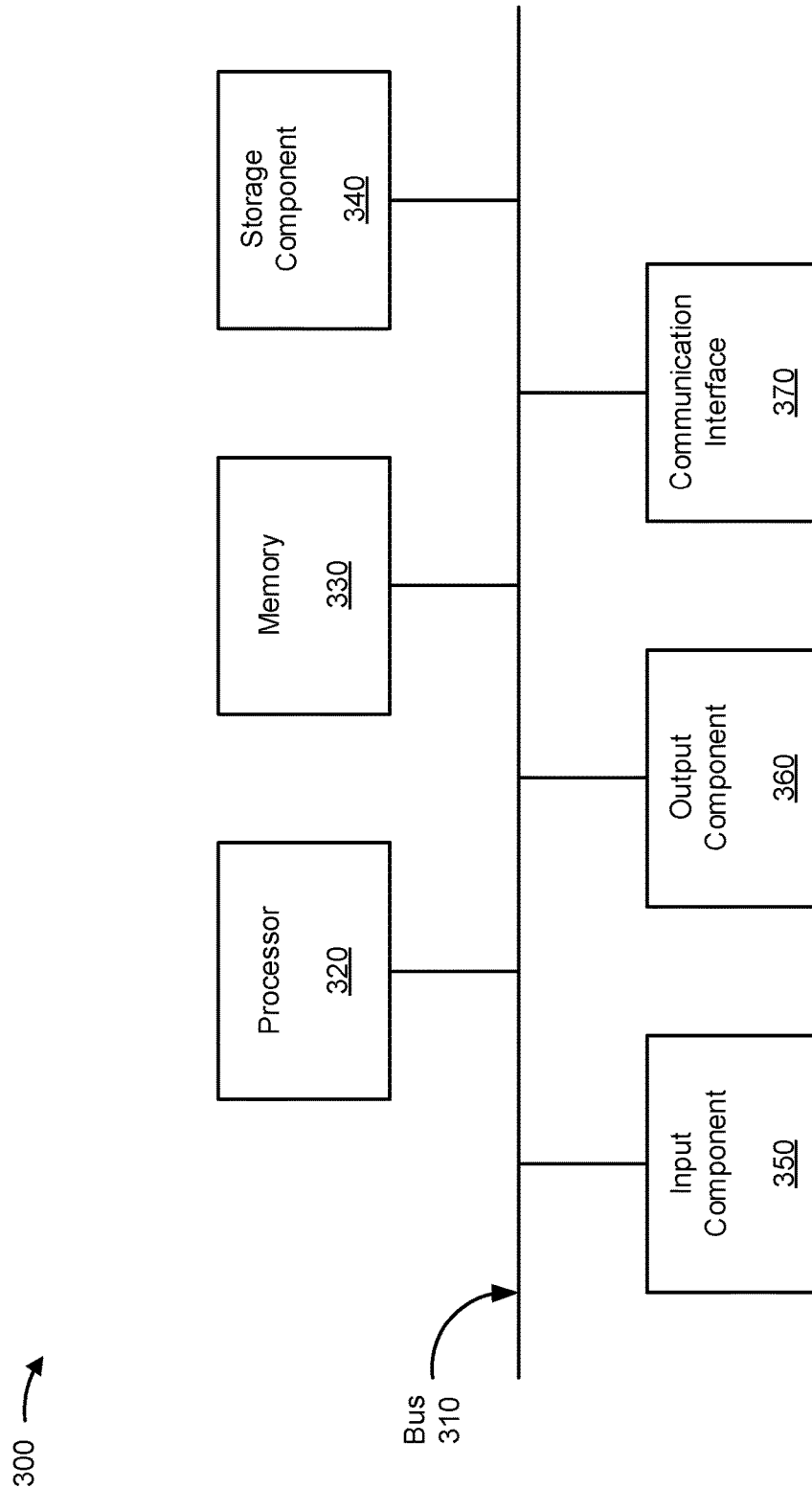
FIG. 3 is a diagram of example components of one or more devices of FIG. 2.

FIG. 3 is a diagram of example components of a device 300. Device 300 may correspond to client device 210, surgical platform 220, and/or computing resource 224. In some implementations, client device 210, surgical platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random-access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
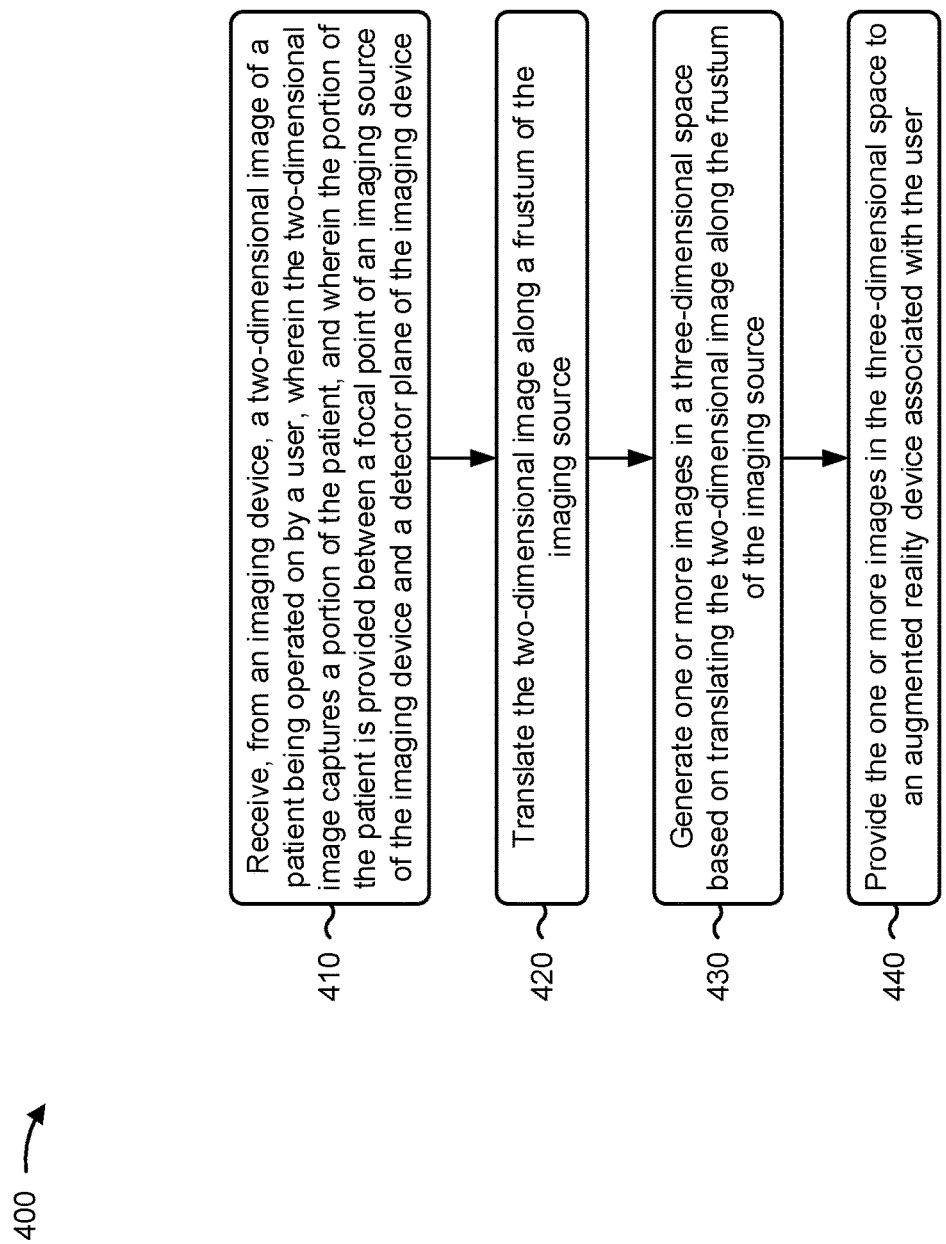

FIG. 4 is a flow chart of an example process 400 for utilizing interactive flying frustums to provide spatially-aware visualization of surgical data in augmented reality. In some implementations, one or more process blocks of FIG. 4 may be performed by a device (e.g., surgical platform 220). In some implementations, one or more process blocks of FIG. 4 may be performed by another device or a group of devices separate from or including the device, such as a client device (e.g., client device 210).

As shown in FIG. 4, process 400 may include receiving, from an imaging device, a two-dimensional image of a patient being operated on by a user, wherein the two-dimensional image captures a portion of the patient, and wherein the portion of the patient is provided between a focal point of an imaging source of the imaging device and a detector plane of the imaging device (block 410). For example, the device (e.g., using computing resource 224, processor 320, communication interface 370, and/or the like) may receive, from an imaging device, a two-dimensional image of a patient being operated on by a user, as described above. In some implementations, the two-dimensional image may capture a portion of the patient, and the portion of the patient may be provided between a focal point of an imaging source of the imaging device and a detector plane of the imaging device.

As further shown in FIG. 4, process 400 may include translating the two-dimensional image along a frustum of the imaging source (block 420). For example, the device (e.g., using computing resource 224, processor 320, memory 330, and/or the like) may translate the two-dimensional image along a frustum of the imaging source, as described above.

As further shown in FIG. 4, process 400 may include generating one or more images in a three-dimensional space based on translating the two-dimensional image along the frustum of the imaging source (block 430). For example, the device (e.g., using computing resource 224, processor 320, storage component 340, and/or the like) may generate one or more images in a three-dimensional space based on translating the two-dimensional image along the frustum of the imaging source, as described above.

As further shown in FIG. 4, process 400 may include providing the one or more images in the three-dimensional space to an augmented reality device associated with the user (block 440). For example, the device (e.g., using computing resource 224, processor 320, memory 330, storage component 340, communication interface 370, and/or the like) may provide the one or more images in the three-dimensional space to an augmented reality device associated with the user, as described above.

Process 400 may include additional implementations, such as any single implementation or any combination of implementations described below and/or in connection with one or more other processes described elsewhere herein.

In a first implementation, the one or more images in the three-dimensional space may correspond to the portion of the patient captured by the two-dimensional image.

In a second implementation, alone or in combination with the first implementation, the augmented reality device may provide an augmented reality view of the one or more images with the two-dimensional image.

In a third implementation, alone or in combination with one or more of the first and second implementations, process 400 may include receiving, from the augmented reality device, a command associated with the one or more images in the three-dimensional space; modifying the one or more images in the three-dimensional space based on the command and to generate one or more modified images in the three-dimensional space; and providing the one or more modified images in the three-dimensional space to the augmented reality device.

In a fourth implementation, alone or in combination with one or more of the first through third implementations, the command may be based on a hand gesture provided by the user, a voice command provided by the user, or a gaze of the user on the one or more images.

In a fifth implementation, alone or in combination with one or more of the first through fourth implementations, process 400 may include calibrating the imaging device prior to receiving the two-dimensional image of the patient.

In a sixth implementation, alone or in combination with one or more of the first through fifth implementations, calibrating the imaging device may include calibrating the imaging device based on a first marker attached to the imaging device and a second marker, and calibrating the imaging device based on changing orientations of the imaging device and the first marker and capturing images associated with the orientations.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
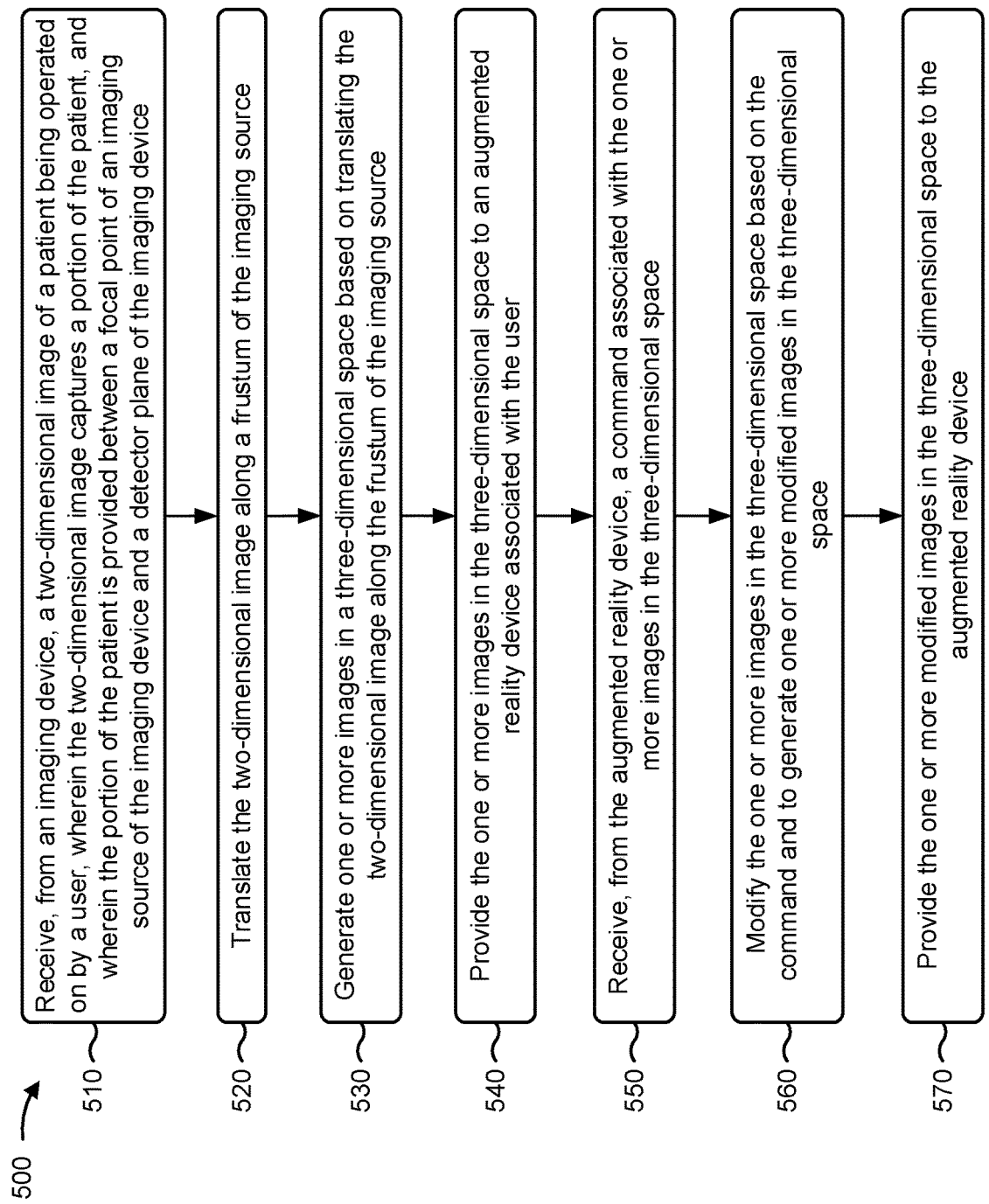

FIG. 5 is a flow chart of an example process 500 for utilizing interactive flying frustums to provide spatially-aware visualization of surgical data in augmented reality. In some implementations, one or more process blocks of FIG. 5 may be performed by a device (e.g., surgical platform 220). In some implementations, one or more process blocks of FIG. 5 may be performed by another device or a group of devices separate from or including the device, such as a client device (e.g., client device 210).

As shown in FIG. 5, process 500 may include receiving, from an imaging device, a two-dimensional image of a patient being operated on by a user, wherein the two-dimensional image captures a portion of the patient, and wherein the portion of the patient is provided between a focal point of an imaging source of the imaging device and a detector plane of the imaging device (block 510). For example, the device (e.g., using computing resource 224, processor 320, communication interface 370, and/or the like) may receive, from an imaging device, a two-dimensional image of a patient being operated on by a user, as described above. In some implementations, the two-dimensional image may capture a portion of the patient, and the portion of the patient may be provided between a focal point of an imaging source of the imaging device and a detector plane of the imaging device.

As further shown in FIG. 5, process 500 may include translating the two-dimensional image along a frustum of the imaging source (block 520). For example, the device (e.g., using computing resource 224, processor 320, memory 330, and/or the like) may translate the two-dimensional image along a frustum of the imaging source, as described above.

As further shown in FIG. 5, process 500 may include generating one or more images in a three-dimensional space based on translating the two-dimensional image along the frustum of the imaging source (block 530). For example, the device (e.g., using computing resource 224, processor 320, storage component 340, and/or the like) may generate one or more images in a three-dimensional space based on translating the two-dimensional image along the frustum of the imaging source, as described above.

As further shown in FIG. 5, process 500 may include providing the one or more images in the three-dimensional space to an augmented reality device associated with the user (block 540). For example, the device (e.g., using computing resource 224, processor 320, memory 330, storage component 340, and/or the like) may provide the one or more images in the three-dimensional space to an augmented reality device associated with the user, as described above.

As further shown in FIG. 5, process 500 may include receiving, from the augmented reality device, a command associated with the one or more images in the three-dimensional space (block 550). For example, the device (e.g., using computing resource 224, processor 320, communication interface 370, and/or the like) may receive, from the augmented reality device, a command associated with the one or more images in the three-dimensional space, as described above.

As further shown in FIG. 5, process 500 may include modifying the one or more images in the three-dimensional space based on the command and to generate one or more modified images in the three-dimensional space (block 560). For example, the device (e.g., using computing resource 224, processor 320, memory 330, and/or the like) may modify the one or more images in the three-dimensional space based on the command and to generate one or more modified images in the three-dimensional space, as described above.

As further shown in FIG. 5, process 500 may include providing the one or more modified images in the three-dimensional space to the augmented reality device (block 570). For example, the device (e.g., using computing resource 224, processor 320, memory 330, storage component 340, communication interface 370, and/or the like) may provide the one or more modified images in the three-dimensional space to the augmented reality device, as described above.

Process 500 may include additional implementations, such as any single implementation or any combination of implementations described below and/or in connection with one or more other processes described elsewhere herein.

In a first implementation, the imaging device may include a C-arm X-ray imaging device.

In a second implementation, alone or in combination with the first implementation, the two-dimensional image of the patient may include a real-time X-ray image of the patient.

In a third implementation, alone or in combination with one or more of the first and second implementations, the one or more images in the three-dimensional space may provide a spatial connection between the portion of the patient and the two-dimensional image.

In a fourth implementation, alone or in combination with one or more of the first through third implementations, process 500 may include receiving, from the augmented reality device, a request to move the two-dimensional image within the frustum; and causing the two-dimensional image to move within the frustum based on the request.

In a fifth implementation, alone or in combination with one or more of the first through fourth implementations, process 500 may include receiving, by the augmented reality device, a selection of a point of the two-dimensional image; and causing the imaging device to move to the point of the two-dimensional image based on the selection.

In a sixth implementation, alone or in combination with one or more of the first through fifth implementations, process 500 may include causing a virtual frustum, that is generated based on the frustum, to be provided to the augmented reality device with the one or more images in the three-dimensional space.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

FIG. 6 is a flow chart of an example process 600 for utilizing interactive flying frustums to provide spatially-aware visualization of surgical data in augmented reality. In some implementations, one or more process blocks of FIG. 6 may be performed by a device (e.g., surgical platform 220). In some implementations, one or more process blocks of FIG. 6 may be performed by another device or a group of devices separate from or including the device, such as a client device (e.g., client device 210).

As shown in FIG. 6, process 600 may include receiving, from an imaging device, a two-dimensional image of a patient being operated on by a user, wherein the two-dimensional image captures a portion of the patient, and wherein the portion of the patient is provided between a focal point of an imaging source of the imaging device and a detector plane of the imaging device (block 610). For example, the device (e.g., using computing resource 224, processor 320, communication interface 370, and/or the like) may receive, from an imaging device, a two-dimensional image of a patient being operated on by a user, as described above. In some implementations, the two-dimensional image captures a portion of the patient. In some implementations, the portion of the patient is provided between a focal point of an imaging source of the imaging device and a detector plane of the imaging device.

As further shown in FIG. 6, process 600 may include translating the two-dimensional image along a frustum of the imaging source (block 620). For example, the device (e.g., using computing resource 224, processor 320, memory 330, and/or the like) may translate the two-dimensional image along a frustum of the imaging source, as described above.

As further shown in FIG. 6, process 600 may include generating one or more images in a three-dimensional space based on translating the two-dimensional image along the frustum of the imaging source (block 630). For example, the device (e.g., using computing resource 224, processor 320, storage component 340, and/or the like) may generate one or more images in a three-dimensional space based on translating the two-dimensional image along the frustum of the imaging source, as described above.

As further shown in FIG. 6, process 600 may include generating a virtual frustum based on the frustum of the imaging source (block 640). For example, the device (e.g., using computing resource 224, processor 320, memory 330, and/or the like) may generate a virtual frustum based on the frustum of the imaging source, as described above.

As further shown in FIG. 6, process 600 may include providing the virtual frustum and the one or more images in the three-dimensional space to an augmented reality device associated with the user (block 650). For example, the device (e.g., using computing resource 224, processor 320, memory 330, storage component 340, communication interface 370, and/or the like) may provide the virtual frustum and the one or more images in the three-dimensional space to an augmented reality device associated with the user, as described above.

Process 600 may include additional implementations, such as any single implementation or any combination of implementations described below and/or in connection with one or more other processes described elsewhere herein.

In a first implementation, process 600 may include receiving, from the augmented reality device, a command associated with the one or more images in the three-dimensional space, wherein the command may be based on a hand gesture provided by the user, a voice command provided by the user, or a gaze of the user on the one or more images; modifying the one or more images in the three-dimensional space based on the command and to generate one or more modified images in the three-dimensional space; and providing the one or more modified images in the three-dimensional space to the augmented reality device.

In a second implementation, alone or in combination with the first implementation, process 600 may include calibrating the imaging device based on a first marker attached to the imaging device and a second marker; and calibrating the imaging device based on changing orientations of the imaging device and the first marker and capturing images associated with the orientations.

In a third implementation, alone or in combination with one or more of the first and second implementations, process 600 may include receiving, from the augmented reality device, a request to move the two-dimensional image within the frustum; and causing the two-dimensional image to move within the frustum based on the request.

In a fourth implementation, alone or in combination with one or more of the first through third implementations, process 600 may include receiving, by the augmented reality device, a selection of a point of the two-dimensional image; and causing the imaging device to move to the point of the two-dimensional image based on the selection.

In a fifth implementation, alone or in combination with one or more of the first through fourth implementations, process 600 may include causing a virtual frustum, that is generated based on the frustum, to be provided to the augmented reality device with the one or more images in the three-dimensional space.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, or a combination of hardware and software.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
    receiving, by a device and from an imaging device, a two-dimensional image of a patient being operated on by a user,
        wherein the two-dimensional image captures a portion of the patient, and
        wherein the portion of the patient is provided between a focal point of an imaging source of the imaging device and a detector plane of the imaging device;
    calibrating, by the device and based on a first marker attached to the imaging device and a second marker, the imaging device,
        wherein the second marker is imaged by an external optical navigation system and the imaging device;
    translating, by the device, the two-dimensional image along a frustum of the imaging source;
    generating, by the device, one or more images in a three-dimensional space based on translating the two-dimensional image along the frustum of the imaging source; and
    providing, by the device, the one or more images in the three-dimensional space to an augmented reality device associated with the user.

2. The method of claim 1, wherein the one or more images in the three-dimensional space correspond to the portion of the patient captured by the two-dimensional image.

3. The method of claim 1, wherein the augmented reality device provides an augmented reality view of the one or more images with the two-dimensional image.

4. The method of claim 1, further comprising:
    receiving, from the augmented reality device, a command associated with the one or more images in the three-dimensional space;
    modifying the one or more images in the three-dimensional space based on the command and to generate one or more modified images in the three-dimensional space; and
    providing the one or more modified images in the three-dimensional space to the augmented reality device.

5. The method of claim 4, wherein the command is based on one or more of:
    a hand gesture provided by the user,
    a voice command provided by the user, or
    a gaze of the user on the one or more images.

6. The method of claim 1, further comprising:
    calibrating the imaging device prior to receiving the two-dimensional image of the patient.

7. The method of claim 1, wherein calibrating the imaging device comprises:
    calibrating the imaging device based on changing orientations of the imaging device and the first marker and capturing images associated with the orientations.

8. A device, comprising:
    one or more memories; and
    one or more processors, communicatively coupled to the one or more memories, configured to:
        receive, from an imaging device, a two-dimensional image of a patient being operated on by a user,
            wherein the two-dimensional image captures a portion of the patient, and
            wherein the portion of the patient is provided between a focal point of an imaging source of the imaging device and a detector plane of the imaging device;
        calibrate, based on a first marker attached to the imaging device and a second marker, the imaging device,
            wherein the second marker is imaged by an external optical navigation system and the imaging device;
        translate the two-dimensional image along a frustum of the imaging source;
        generate one or more images in a three-dimensional space based on translating the two-dimensional image along the frustum of the imaging source;
        provide the one or more images in the three-dimensional space to an augmented reality device associated with the user;
        receive, from the augmented reality device, a command associated with the one or more images in the three-dimensional space;
        modify the one or more images in the three-dimensional space based on the command and to generate one or more modified images in the three-dimensional space; and
        provide the one or more modified images in the three-dimensional space to the augmented reality device.

9. The device of claim 8, wherein the imaging device includes a C-arm X-ray imaging device.

10. The device of claim 8, wherein the two-dimensional image of the patient includes a real-time X-ray image of the patient.

11. The device of claim 8, wherein the one or more images in the three-dimensional space provide a spatial connection between the portion of the patient and the two-dimensional image.

12. The device of claim 8, wherein the one or more processors are further configured to:

receive, from the augmented reality device, a request to move the two-dimensional image within the frustum; and cause the two-dimensional image to move within the frustum based on the request.

13. The augmented reality device of claim 8, wherein the one or more processors are further configured to:

receive, by the augmented reality device, a selection of a point of the two-dimensional image; and cause the imaging device to move to the point of the two-dimensional image based on the selection.

14. The device of claim 8, wherein the one or more processors are further configured to:

cause a virtual frustum, that is generated based on the frustum, to be provided to the augmented reality device with the one or more images in the three-dimensional space.

15. A non-transitory computer-readable medium storing instructions, the instructions comprising:

one or more instructions that, when executed by one or more processors of a device, cause the one or more processors to:

receive, from an imaging device, a two-dimensional image of a patient being operated on by a user, wherein the two-dimensional image captures a portion of the patient, and wherein the portion of the patient is provided between a focal point of an imaging source of the imaging device and a detector plane of the imaging device;

calibrate, based on a first marker attached to the imaging device and a second marker, the imaging device, wherein the second marker is imaged by an external optical navigation system and the imaging device;

translate the two-dimensional image along a frustum of the imaging source;

generate one or more images in a three-dimensional space based on translating the two-dimensional image along the frustum of the imaging source;

generate a virtual frustum based on the frustum of the imaging source; and provide the virtual frustum and the one or more images in the three-dimensional space to an augmented reality device associated with the user.

16. The non-transitory computer-readable medium of claim 15, wherein the one or more instructions, when executed by the one or more processors, further cause the one or more processors to:

receive, from the augmented reality device, a command associated with the one or more images in the three-dimensional space, wherein the command is based on one or more of:
  a hand gesture provided by the user,
  a voice command provided by the user, or
  a gaze of the user on the one or more images;

modify the one or more images in the three-dimensional space based on the command and to generate one or more modified images in the three-dimensional space; and provide the one or more modified images in the three-dimensional space to the augmented reality device.

17. The non-transitory computer-readable medium of claim 15, wherein the one or more instructions, when executed by the one or more processors, further cause the one or more processors to:

receive, from the augmented reality device, a request to move the two-dimensional image within the frustum; and cause the two-dimensional image to move within the frustum based on the request.

18. The non-transitory computer-readable medium of claim 15, wherein the one or more instructions, when executed by the one or more processors, further cause the one or more processors to:

receive, by the augmented reality device, a selection of a point of the two-dimensional image; and cause the imaging device to move to the point of the two-dimensional image based on the selection.

19. The non-transitory computer-readable medium of claim 15, wherein the one or more instructions, when executed by the one or more processors, further cause the one or more processors to:

cause a virtual frustum, that is generated based on the frustum, to be provided to the augmented reality device with the one or more images in the three-dimensional space.

20. The non-transitory computer-readable medium of claim 15, wherein the one or more instructions, when executed by the one or more processors, further cause the one or more processors to:

calibrate the imaging device based on changing orientations of the imaging device and the first marker and capturing images associated with the orientations.

\* \* \* \* \*